United States Patent [19]

Schmitz-Josten et al.

[11] 4,177,563

[45] Dec. 11, 1979

[54] DENTAL FILLING MATERIAL

[75] Inventors: Robert Schmitz-Josten, Cologne; Manfred Borgardt, Wuppertal; Hans-Hermann Schulz, Leichlingen; Michael Walkowiak, Cologne; Bernhard Leusner, Leverkusen; Carlhans Süling, Odenthal, all of Fed. Rep. of Germany

[73] Assignee: Bayer Aktiengesellschaft, Leverkusen, Fed. Rep. of Germany

[21] Appl. No.: 907,639

[22] Filed: May 19, 1978

[30] Foreign Application Priority Data

Jun. 25, 1977 [DE] Fed. Rep. of Germany ....... 2728764

[51] Int. Cl.² .......................... C08K 3/22; C08K 3/34; C08K 3/36
[52] U.S. Cl. .............................. 433/228; 260/42.52; 260/998.11
[58] Field of Search ....................... 260/998.11, 42.52

[56] References Cited

U.S. PATENT DOCUMENTS

| 3,808,170 | 4/1974 | Rogers | 260/998.11 X |
| 3,862,920 | 1/1975 | Foster et al. | 260/998.11 X |
| 3,971,754 | 7/1976 | Jurecic | 260/998.11 X |

Primary Examiner—Sandra M. Person
Attorney, Agent, or Firm—Sprung, Felfe, Horn, Lynch & Kramer

[57] ABSTRACT

The invention includes formulated dental filling materials comprising a polymerizable organic plastics material containing inorganic fillers, which filling material comprises at least two pastes in intimate admixture with one another in a paste/paste system in which hardening is initiated by means of a peroxidic initiator and an accelerator, wherein said at least two pastes contain different inorganic fillers with different chemical constitutions such that one of said at least two pastes contains filler with a substantially higher proportion of elements with high atomic number than does the other of said at least two pastes. Also included in the invention is a dental filling pack containing said formulated dental filling materials as well as a method for their use.

12 Claims, No Drawings

DENTAL FILLING MATERIAL

The present invention relates to formulated dental filling materials, based on organic plastics material containing inorganic filler, suitable for use in paste/paste systems.

Dental filling compositions based on organic plastics material filled with inorganic filler are known from U.S. Pat. No. 3,066,112. In contrast to conventional organic plastics material provided with inorganic filler, the organic plastics material containing filler for use in dentistry must satisfy certain processing criteria which are practicable and customary in dental practice. In addition, the mechanical properties of the hardened filling material products should remain substantially unchanged for years, even in the oral environment, and the products must be highly compatible both with the mucous membrane of the mouth and with the dental tissue.

An example of a suitable inorganic filler according to U.S. Pat. No. 3,066,112 is silanized quartz glass, to which flint-glass powder can be added as a filler component in order to achieve X-ray opacity. Isopropylidene-bis-/p-phenyleneoxy (2-hydroxy-trimethylene)/-dimethacrylate (="bis-GMA") mixed with a reactive diluent is used as the organic "binder".

The disadvantage of dental filling compositions of this type is that they are used in a powder/liquid system, which is difficult and inconvenient to handle. The proportion of filler to organic binder is not automatically constant in this kind of application form; thus not only are different mechanical properties obtained in individual fillings from one case to the next and are seldom optimum, but also the polymerization shrinkage during the hardening of the filling is not automatically set at the low level required clinically.

It is also known to use dental filling compositions, based on organic plastic material containing inorganic filler, for application in paste/paste system. Thus, U.S. Pat. No. 3,926,906 and DT-AS (German Published Specification) No. 1,929,831 describes how system of this type, which produce clinically useful fillings, can be built up. In this case it is an essential characteristic of such paste/paste systems that the "catalyst paste" and the "activator paste" should have substantially the same composition from the point of view of the chemical composition of the components, with the proviso the constituents of the pastes which are only present in small amounts, such as, for example, different dye-stuff additives or catalyst/activator components which differ chemically, should be distributed evenly throughout the pastes.

This system indeed has on the one hand the advantage that the mixing process can be carried out particularly easily, but on the other hand it has the disadvantage that a graded X-ray opacity, such as is desirable in many cases for dental filling compositions and frequently is also necessary, cannot be obtained since the filling has a constant X-ray absorption, independently of the mixing ratio, because the pastes are built up chemically in the same manner. It is therefore not possible to adjust the intensity of the X-ray opacity by varing the mixing ratio of the activator paste and catalyst paste.

However, a graded X-ray opacity is desirable, depending on the extent and volume of the dental fillings. It, for example, a tooth is built up extensively by dental filling materials based on organic plastics material containing inorganic filler, a relatively low X-ray opacity is desired so that the extent of the hard tooth tissue substance or of the composite structure can be readily ascertained on an X-ray photograph during later prosthetic work, for example the fitting of a crown. On the other hand, fillings of relatively low volume, such as, for example, fillings in the neck of a tooth, require a higher X-ray opacity so that the filling can be readily identified.

A further disadvantage of paste/paste systems in which the pastes are identical from the point of view of the main chemical composition of the components and the proportions of the components is that the catalyst pastes always have a limited and varying shelf life if these pastes contain a filler which causes a relatively high content of elements with high atomic numbers. Even in low amounts, however, the ions of elements with relatively high atomic numbers can cause catalytic decomposition of peroxides.

The present invention provides formulated dental filling material comprising a polymerizable organic plastics material containing inorganic filler, which filling material comprises at least two pastes in intimate admixture with one another in a paste/paste system in which hardening is initiated by means of a peroxidic initiator, wherein said at least two pastes contain different inorganic fillers with different chemical constitutions such that one of said at least two pastes contains filler with a substantially higher proportion of elements with high atomic number than does the other of said at least two pastes.

It is surprising that the pastes according to the invention, in which the fillers used in the individual pastes differ substantially in their chemical composition, can be processed without additional measures so as to produce homogeneous dental fillings in the same way as pastes which are essentially built up from chemically identical fillers and which indeed have a good tolerance towards the substrate alone, but do not enable the X-ray opacity to be adjusted to the clinically desired value by way of the mixing process.

Formulated dental filling materials based on organic plastics material containing inorganic filler are understood as compositions which are ready for use, that is to say which have all the useful characteristic parameters necessary for adjusting the clinically relevant properties to the required properties, all the useful characteristic parameters necessary for adjusting the aesthetic characteristics as desired and all the useful characteristic parameters required for their application.

Suitable materials include, in particular, those organic plastics materials which are formed from low-molecular monomers by vinyl polymerization and/or optionally by polyisocyanate polyaddition, with hardening, and in which a substantial proportion of the whole hardened composition consists of inorganic fillers. The organic chemical component of the pastes which can be hardened, is also called a "binder".

Clinically relevant properties are firstly the required mechanical strength, and furthermore adequate stability in the oral cavity environment, a sufficient X-ray opacity and good inertness towards dental tissue and the surrounding mucous membranes.

Desired aesthetic characteristics are to be understood herein as, inter alia, the properties which enable the colour and surface structure to be matched as well as possible to that of the teeth to be filled. The colour adjustment may be effected firstly by adding dyestuffs in small amounts; secondly, however, the required colour can also be imparted by using materials of greater or less transparency, which after hardening together ensure that, as a result of their partial transparency, the colour of the filling gives the appearance of being matched with the original colour of the tooth.

Useful characteristic parameters required for the application of the material are understood herein as the characteristic parameters such as the processing time, hardening time, mixing time an consistency of the pastes and of the paste/paste mixtures.

The known isocyanates and the compounds which are active in a Zerewitinoff reaction and are suitable for polyisocyanate polyaddition, such as primary and secondary amines, hydrazine derivatives and/or polyalcohols, are suitable for use in a hardening procedure involving a polyisocyanate polyaddition.

Monomers which can be hardened by vinyl polymerisation are compounds which contain at least one polymerisable carbon double bond. Those monomers which are polyfunctional with respect to the double bonds, that is to say which lead to highly crosslinked polymers or copolymers, are particularly suitable for building up the organic plastics material according to the invention.

Examples of suitable monomers are methacrylic acid esters or acrylic acid esters of aliphatic, such as alkyl or aromatic, such as monocyclic carbocyclic polyols, for example ethylene glycol dimethacrylate, diethylene glycol dimethacrylate or triethylene glycol dimethacrylate or the corresponding acrylic acid ester, and also compounds such as trimethylolpropane trimethacrylate, triacrylylformal, or the methacrylic acid esters of bisphenol A or derivatives thereof, such as, for example, Bis-GMA, or the bis-(methacrylic acid ester) of the bis-(2-hydroxyethyl ether) of bis-phenol A. Examples of further monomers which are suitable for building up the dental filling compositions according to the invention are those which are known from U.S. Pat. No. 3,179,623, U.S. Pat. No. 3,730,947 or from DT-OS (German Published Specification) No. 2,419,887. The formulae of examples of suitable comonomers are listed in the following summary in which the symbols have the following meanings:

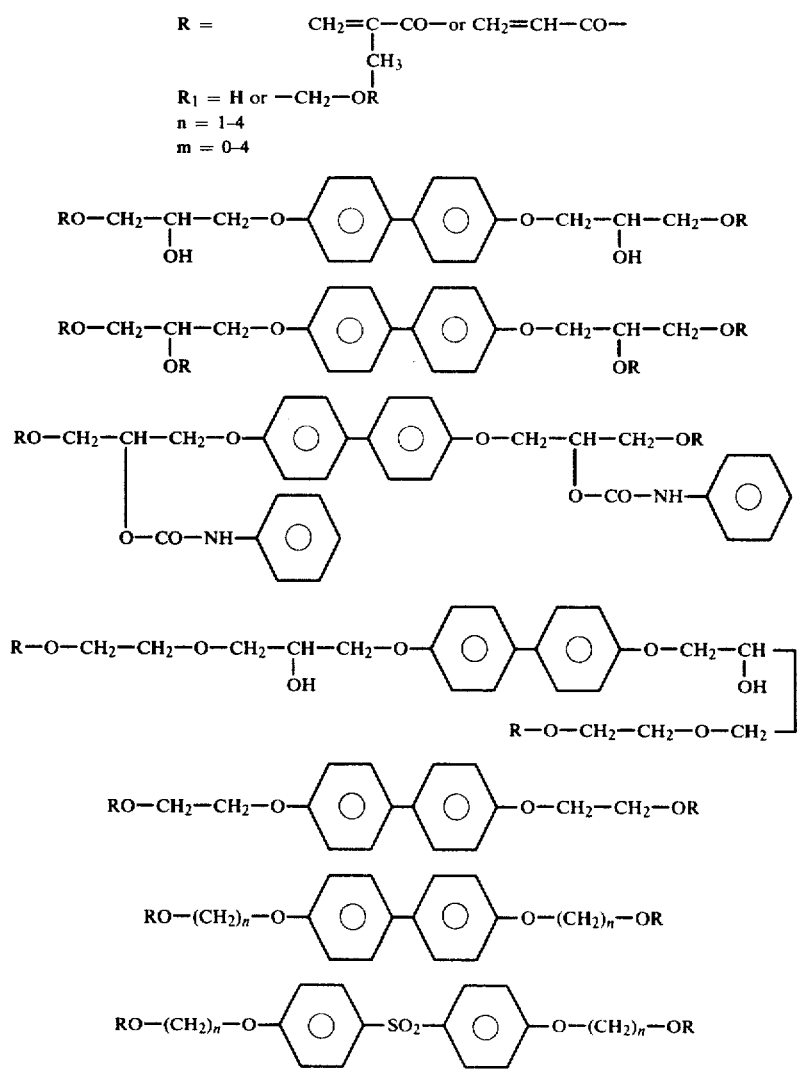

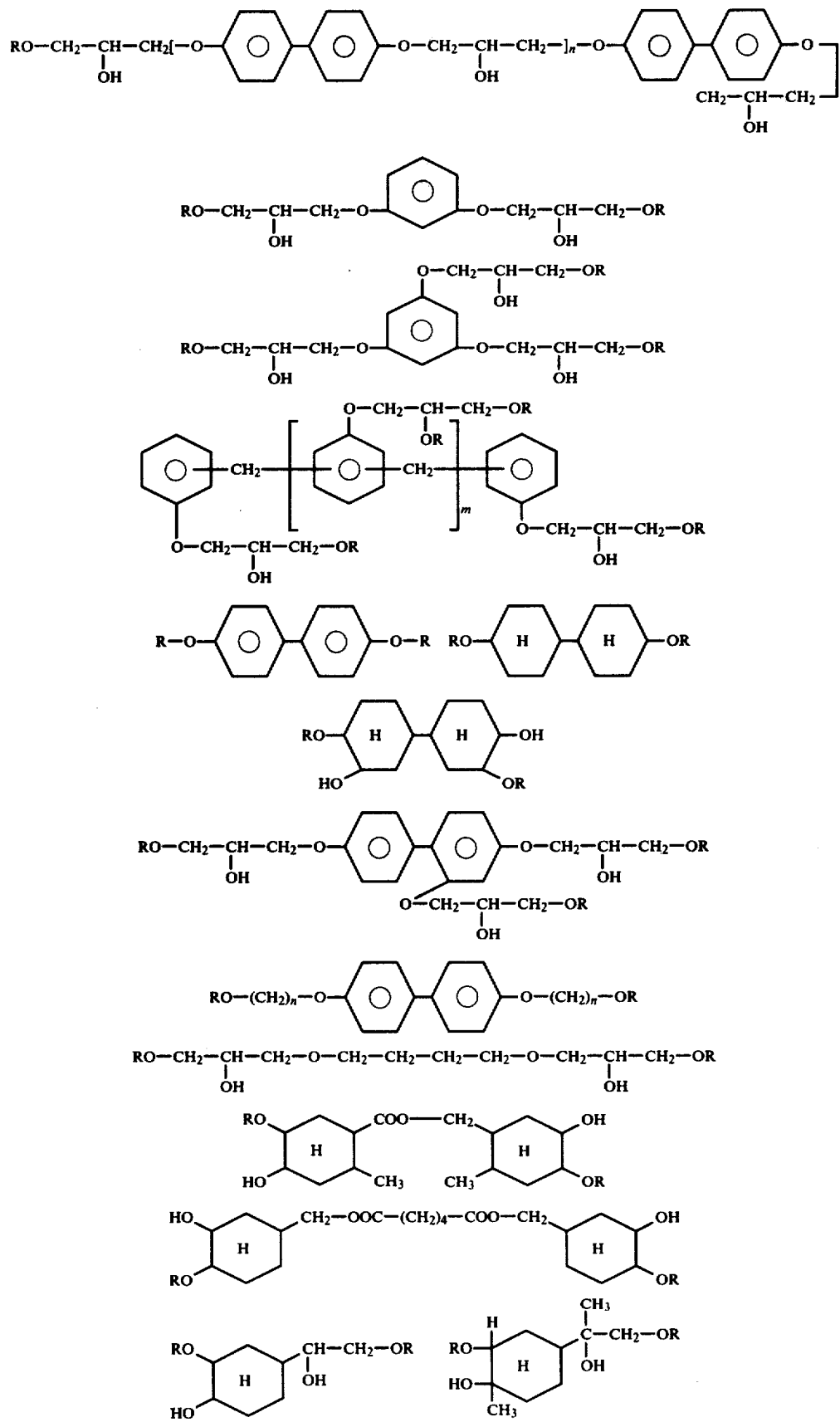

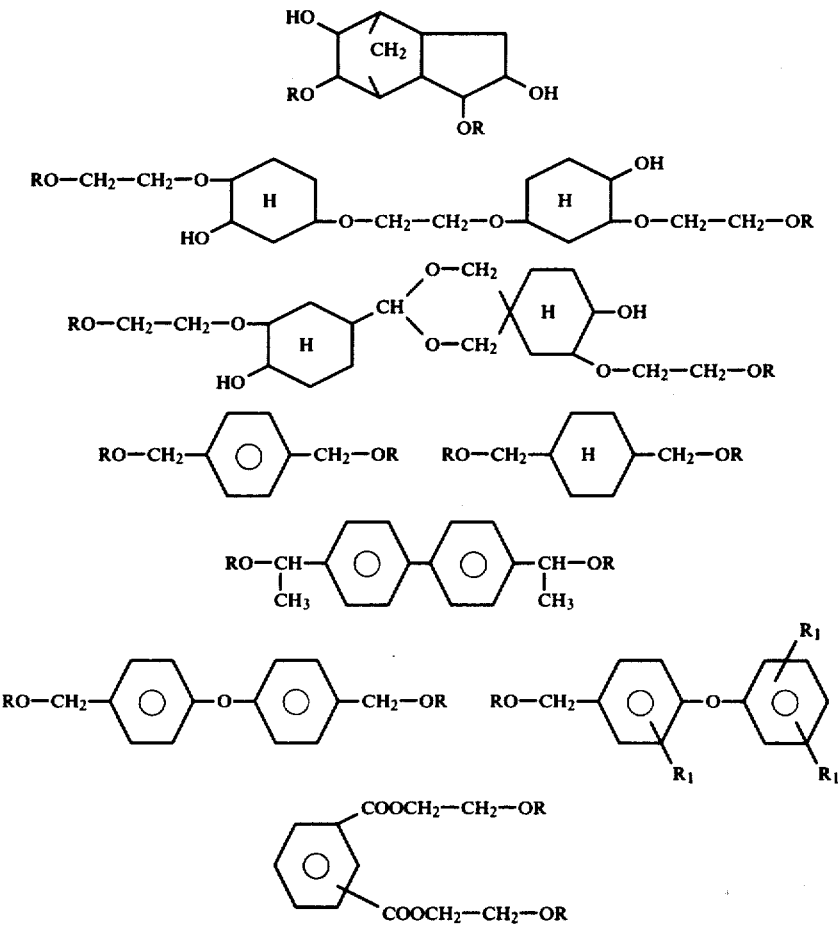
in the ortho-, meta- or para-form. A compound of the general formula:
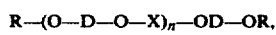
wherein
HO—D—OH is a polyol and
HO—X—OH is a dicarboxylic acid, and in particular a saturated or unsaturated, cyclic or acyclic polyol and dicarboxylic acid.
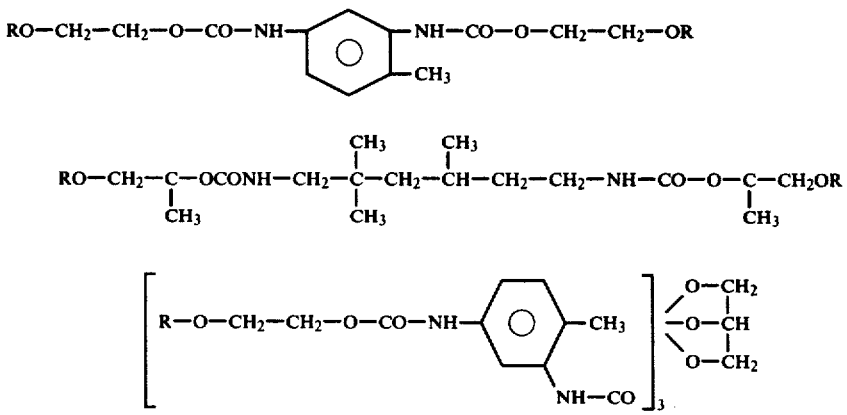
(average molecular weight 2,500)

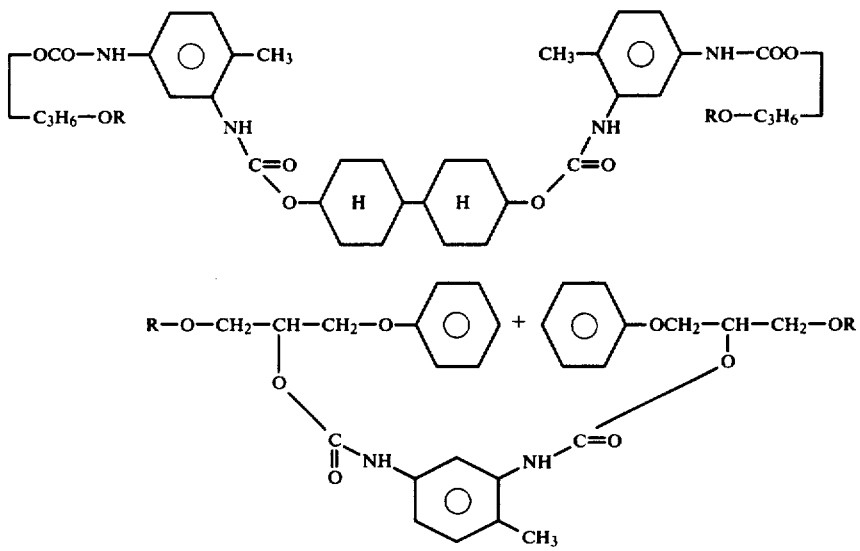

and prepolymers containing NCO and urethane groups, reacted with hydroxyalkyl methacrylate according to DT-OS (German Published Specification) No. 2,419,887 or French Pat. No. 2,271,807.

In many cases it is particularly advantageous to use a mixture of different monomers as the binder for mixing with the inorganic filler for the preparation of the pastes. Mixing enables, for example, on the one hand the refractive index of the resulting plastic to be matched with that of the inorganic fillers and sufficient transparency of the finished fillings thus ensured, and on the other hand pastes having the desired viscosity and consistency may be prepared relatively easily using mixtures of different organic monomers. A preferred embodiment of the dental filling material according to the invention contains a mixture of polymerisable derivatives of bis-phenol A and dimethacrylates of aliphatic, particularly alkane, diols, such as, for example, ethylene glycol, butane-1,4-diol, hexane-1,6-diol, diethylene glycol or triethylene glycol, as the binder. As already mentioned it is preferred to initiate the curing of the dental filling compositions by an activating system consisting of a suitable peroxidic catalyst such as benzoyl peroxide and an activator such as N,N-dimethylparatoluidine and paratoluenesulfinic acid. Other suitable activators are described, for example, in the U.S. Pat. Nos. 2,558,139, 3,541,068, 3,926,906 and 3,359,533. By mixing the catalyst containing paste with the activator containing paste, radicals are generated which start the polymerization of the monomers called binders.

Suitable inorganic fillers for the dental filling material according to the invention are on the one hand products such as rock crystal, quartzite, cristobalite or $Al_2O_3$, which contain no elements with relatively high atomic numbers which may catalyze degradation of peroxides, such as, for example, Cu, Fe, Pb, Bi, Sn and Zn, and which also contain, for example, only traces of less than 2.0% of the elements Ba or La. On the other hand, however, fillers in the form of glasses or glass ceramics, which contain a high proportion of elements which absorb X-rays well or scatter them considerably, are suitable for use as a filler for the paste containing no peroxidic catalyst. The use of glasses containing, for example, Ba as a component of inorganic fillers is described in detail, for example, in U.S. Pat. No. 3,808,170, with the proviso in that case that both the peroxidic catalyst paste and the activator paste contain this filler in equal amounts. Further inorganic fillers which are suitable agents for absorbing X-rays are described, for example, in DT-OS (German Published Specification) No. 2,347,591. The glass ceramics described in this application contain La and Zr as elements which cause relatively intensive absorption of the X-ray radiation.

These glass ceramics are furthermore distinguished by a particularly favourable coefficient of thermal expansion.

The filler may be processed by a grinding operation so as to produce a fine-particled powder, and the average particle size should be from 1 to 150 micron. In some cases addition of glass beads with a particle size $<40\mu$ (for example Reflexperlen RPG 22® from Jenaer Glaswerke Schott u. Gen. (Western Germany) give the pastes a good processability it has to be treated with a organosilane keging agent. Addition of highly dispersed submicron silica in amounts of about 2%, relative to the amount of total filler, are suitable in some cases for keeping the consistency of the paste constant over a relatively long period because settling of the coarser filler is delayed by highly disperse additives of this type.

The preparation of the pastes by mixing the binders and the fillers can be carried out in the laboratory on glass or porcelain plates or in glass or porcelain containers. The pastes are prepared on an industrial scale using automatically operated mixing units, of which the following may be mentioned as examples: JEL 25/53 mulling machine from Messrs. Engelmann, Ludwigshafen; RMO type mortar mill from Messrs. Retsch KG, Haan; a high-speed micro-mill from Messrs. Retsch KG, Haan; ball mill from Staatliche Porzellan Manufaktur Berlin; "Pulverisette 5" planetary ball mill from Messrs. A Fritsch, Idar-Oberstein; planetary mixer from Messrs. Drais, Mannheim; planetary mixer from Messrs. Spangenberg, Mannheim; kneader from Messrs. Werner & Pfleiderer, Stuttgart; kneader from Messrs. Meili, Zurich; mixer from Messrs. Lodige, Paderborn; and mixer from Messrs. AMK, Aachen.

Roll mills, such as, for example, the "Exakt 50" triple roll mill from Messrs. O. Herrrmann, Norderstedt, can also be advantageously used fro the final homogenisation.

The proportions of filler to binder in the pastes are limited on the one hand by the desired consistency; it must be easy to introduce the pastes into cavities and this means that too high a content of inorganic fillers is precluded. On the other hand, a high hardness is required of the hardened filling and in addition the shrinkage caused by the hardening should be as low as possible. Both requirements are best fulfilled when the porportion of filler is as high as possible. In general, pastes which contain from 55 to 85%, preferably from 60 to 80%, of filler are used.

EXAMPLE 1

22.19 parts by weight of a mixture of 64% bisphenol A diglycidyl dimethacrylate and 36% triethylene glycol dimethacrylate, containing as an amine activator 1,2% N,N-di(2-hydroxylethyl)-p-toluidine, are initially introduced into a "Pulverisette 5" planetary ball mill (Messrs. Alfred Fritsch). The ball mill is provided with agate cups and agate balls. 9.59 parts by weight of finely ground α-quartz (rock crystal), which has been treated with 0.4% of γ-methacryloxypropyl-trimethoxysilane, relative to the quartz, are added to the mixture. 66.74 parts by weight of barium-containing glass powder Schott 8235 ® (Messrs. Jenaer Glaswerke Schott und Gen.), which has also been treated with 0.4% of the same silane, relative to the glass, are also added. 1.48 parts by weight of highly disperse silica HDK 15 P ® (Messrs. Wacker Chemie) are added in order to adjust the consistency of the paste. The colour of the composite paste is adjusted by adding 10 ppm of Irgazingelb 3 RLT, 16 ppm of Helioechtgelb ER, 2.2 ppm of Makrolexrot G and 0.3 ppm of Makrolexrot 5 B. A kneadable composite paste which is designated Paste A is obtained in the planetary ball mill within a mixing time of 20 minutes.

20.18 parts by weight of the same mixture of bisphenol A diglycidyl dimethacrylate and triethylene glycol dimethacrylate, to which 2% of benzoyl peroxide has been added, are initially introduced into a separate agate cup in the planetary ball mill, to make a paste activated with benzoyl peroxide (Paste B). 78.47 parts by weight of finely ground (-quartz (rock crystal), which has been silanized with 0.4% of γ-methacryloxypropyltrimethoxysilane, relative to the quartz, are added to the mixture. 1.35 parts by weight of highly disperse silica HDK 15 P are also added. A kneadable composite paste (Paste B) results after a mixing time of 20 minutes.

Paste A and Paste B are mixed with one another in a weight ratio of 1:1. Cylindrical test pieces with a diameter of 6 mm and a height of 12 mm are prepared from the mixture in accordance with FDI Specification No. 5 and have, after storing in water at 37° C. for 24 hours, a compressive strength of 210 n/mm².

Test pieces consisting of the same mixture and having the dimensions 25 mm×2 mm×2 mm, which are prepared in accordance with DIN draft specification OO 13 921, have, after storage in distilled water at 37° C. for 24 hours, a flexural strength of 82 N/mm².

Comparative storage experiments on composite pastes containing benzoyl peroxide 3 g of benzoyl peroxide and 0.2 g of 2,6-di-t-butyl-4-methylphenyol are dissolved in a mixture of 64 g of bisphenol A diglycydyl methacrylate and 36 g of triethylene glycol dimeth-acrylate at room temperature. This solution is then mixed, in the percentage indicated, with the X-ray-opaque silanized fillers indicated in the Table which follows and the mixture is weighed into polyethylene containers and stored in a drying cabinet at 40° C.

The peroxide content is determined at time intervals of about 1 week and is calculated as a percentage of the initial value of 100.

The filler-free peroxide solution and a paste prepared with silanized rock crystal powder are included in the test as a control.

Table

| Decrease in the peroxide content on storage at 40° C. | | | | | | | | | |
|---|---|---|---|---|---|---|---|---|---|
| Solution without filler | 0 | 5 | 12 | 19 | 26 | 33 | 40 | 47 | Days |
|  | 100% | 94.9% | 93.6% | 92.1% | 88.4% | 87.1% | 84.8% | 83.85% | benzoyl peroxide |
| Paste containing 78.3% of silanised rock crystal | 0 | 5 | 12 | 19 | 26 | 33 | 40 | 47 | 61 Days |
|  | 100% | 96.7% | 94.5% | 90.0% | 88.1% | 82.0% | 81.7% | 81.7% | 82.0% benzoyl peroxide |
| Paste containing 73.2% of Ba-glass Schott++8235 ® | 0 | 7 | 14 | 23 | Days |  |  |  |  |
|  | 100% | 91.6% | 80.6+% | 85.8+% | benzoyl peroxide |  |  |  |  |
| Paste containing 75% of La-glass Schott P 1816 ® | 0 | 7 | 14 | 23 | Days |  |  |  |  |
|  | 100% | 53.7+% | 42.2+% | 37.0+% | benzoyl peroxide |  |  |  |  |
| (prepared according to DT-OS (German Published Specification) 2,347,591) |  |  |  |  |  |  |  |  |  |
| Paste containing 81% of Ba-glass from Messrs. | 0 | 7 | 14 | 23 | Days |  |  |  |  |
|  | 100% | 66.1+% | 31.1+% | 18.5+% | benzoyl peroxide |  |  |  |  |
| Kimble+++ Ray Sorb T 3000 ® |  |  |  |  |  |  |  |  |  |

+ partially polymerised
++ Messrs. Schott Gen., Mainz, Western Germany
+++ Messrs. Kimble O-I, Toledo, Ohio, U.S.A. (Division of Owens-Illinois, U.S.A.)

What is claimed is:

1. A formulated dental filling material comprising a polymerizable organic plastics material containing inorganic fillers, which filling material comprises at least two pastes in intimate admixture with one another in a paste/paste system in which hardening is initiated by means of a peroxidic initiator and an accelerator, wherein said at least two pastes contain different inorganic fillers with different chemical constitutions such that one of said at least two pastes contains filler with a substantially higher proportion of elements with high atomic number than does the other of said at least two pastes.

2. Formulated dental filling material as claimed in claim 1 in which the polymerizable organic plastics material is one which hardens by means of vinyl polymerization and/or polyisocyanate polyaddition.

3. Formulated dental filling material as claimed in claim 1 or claim 2 which contains a mixture of polymerizable derivatives of bisphenol A and dimethacrylates of aliphatic glycols as binder.

4. Formulated dental filling material as claimed in any one of claims 1, 2 or 3 wherein each of the pastes contains from 55 to 85%, by weight of filler.

5. Formulated dental filling material as claimed in claim 4 wherein each of the pastes contain from 60 to 80% by weight of filler.

6. Formulated dental filling material according to claim 1 in which one of said at least two pastes contains the peroxidic initiator and the other paste contains an accelerator.

7. Formulated dental filling material according to claim 6 in which the peroxidic initiator is benzoyl peroxide.

8. Formulated dental filling material according to claim 1 in which the filler in said one of the at least two pastes with the higher proportion of elements with high atomic number comprises at least one of a glass or glass ceramic, containing a high proportion of elements which absorb X-rays well or scatter them considerably.

9. A formulated dental filling material according to claim 8 in which the filler in the other of said at least two pastes comprises at least one of rock crystal, quartzite, cristobalite or $Al_2O_3$.

10. A dental filling material pack in which said material comprises a polymerizable organic plastics material containing inorganic filler, said pack comprising at least two pastes usable together in a paste/paste system, in which hardening is initiated by means of a peroxidic initiator and an accelerator, for forming dental fillings, wherein one of said at least two pastes contains inorganic filler with a substantially higher proportion of elements with high atomic number than does the other of said at least two pastes.

11. A dental filling material pack according to claim 10 in which said other of said at least two pastes contains the peroxidic initiator.

12. A method for filling cavities in teeth which comprises applying to said cavities a formulated dental filling material of claim 1.

* * * * *